United States Patent
Hwang

(10) Patent No.: US 9,662,443 B2
(45) Date of Patent: May 30, 2017

(54) ALERT DEVICE FOR INTRAVENOUS DRIP

(71) Applicant: Richard Hwang, New Taipei (TW)

(72) Inventor: Richard Hwang, New Taipei (TW)

( * ) Notice: Subject to any disclaimer, the term of this patent is extended or adjusted under 35 U.S.C. 154(b) by 577 days.

(21) Appl. No.: 14/147,779

(22) Filed: Jan. 6, 2014

(65) Prior Publication Data

US 2015/0190571 A1    Jul. 9, 2015

(51) Int. Cl.
*A61M 5/168* (2006.01)
*G01F 23/26* (2006.01)
*A61M 5/14* (2006.01)
*G01F 23/24* (2006.01)

(52) U.S. Cl.
CPC ........ *A61M 5/1684* (2013.01); *A61M 5/1411* (2013.01); *G01F 23/268* (2013.01); *A61M 5/1689* (2013.01); *A61M 2205/14* (2013.01); *A61M 2205/18* (2013.01); *A61M 2205/3317* (2013.01); *G01F 23/242* (2013.01)

(58) Field of Classification Search
CPC ........ A61M 5/1684; A61M 2205/3317; A61M 2205/18; G01F 23/24; G01F 23/242; G01F 23/268
USPC ........................................... 604/253
See application file for complete search history.

(56) References Cited

U.S. PATENT DOCUMENTS

| | | | | |
|---|---|---|---|---|
| 3,641,543 A | * | 2/1972 | Rigby | A61M 5/1684 |
| | | | | 128/DIG. 13 |
| 4,984,462 A | * | 1/1991 | Hass, Jr. | A61M 5/14 |
| | | | | 250/577 |
| 2006/0241552 A1 | * | 10/2006 | Tang | A61M 5/1684 |
| | | | | 604/253 |
| 2011/0015583 A1 | * | 1/2011 | Davis | A61M 5/1689 |
| | | | | 604/253 |

* cited by examiner

*Primary Examiner* — Theodore Stigell
*Assistant Examiner* — Benjamin Koo

(57) ABSTRACT

An alert device for use with an intravenous drip, comprises two induction ends and a control unit. The control unit comprises a circuit module, an alarm module and a power module. The two induction ends are located on a pipe of the intravenous drip and are contacting with an injection solution inside the pipe. The two induction ends are electrically connected to the control unit by wires. The circuit module detects the induction ends to determine whether the induction ends are in an open-loop status or not. The circuit module connects to the alarm module. The power module supplies power for the control unit. The induction ends uses the injection solution as a conducting means to form an electrically closed loop; when the induction ends do not contact with the injection solution, the induction ends become an open-loop, and thus the alarm module generates alarm signals.

4 Claims, 4 Drawing Sheets

ALERT DEVICE FOR INTRAVENOUS DRIP

BACKGROUND OF THE INVENTION (1) Field of the Invention

The present invention refers to an alert device for intravenous drip, especially for an alert device which can generate alarm signals when the intravenous drip is going to run out of injection solution.

(2) Description of the Prior Art

During the past years, biomedical testing systems gain more and more attentions by nursing facilities. However, when a patient is suffering from an intravenous drip, there must be another person such as a relative of that patient or a nurse taking care of the amount of injection solution left in that intravenous drip, in order to avoid the intravenous drip running out of injection solution. Otherwise, once the intravenous drip runs out of injection solution, either the patient's blood would flow into the pipe of intravenous drip, or the air might enter the patient's blood vessels and causing embolisms problems. And thus, monitoring the amount of injection solution left inside the intravenous drip becomes a safety issue of nursing facilities.

The present invention provides an alert device for intravenous drip, which uses electric current loop to monitor the remaining amount of injection solution within the intravenous drip, and uses a control unit to determine the signals from the electric current loop so as to detect automatically whether or not the injection solution is going to run out soon. In addition, when the injection solution is going to run out soon, an alarm module generates alarms and also transmits alarm signals to the nursing department. In addition to inform nurses to take care of this intravenous drip, the alert device of the present invention can also save laboring since the nurses won't need to check the remaining amount of injection solution from time to time. An therefore the nurses can have more time to rest or do other jobs, so as to increase the efficiency and quality of nursing services.

SUMMARY OF THE INVENTION

The primary objective of the present invention is to provide an alert device for intravenous drip, which can generate alarm signals automatically when the intravenous drip is going to run out of injection solution.

In order to achieve the aforementioned objective, the present invention provides an alert device which is attachable to a dripping pipe of an intravenous drip. The dripping pipe is able to contain an injection solution. The alert device comprises: at least two induction ends and a control unit. The two induction ends are furnished on the dripping pipe and contactable with the injection solution. The control unit is coupled with the induction ends and further comprises: a circuit module, an alarm module and a power module. The circuit module is coupled with the induction ends for detecting whether the induction ends are in an open-loop status or a close-loop status. The alarm module is coupled with the circuit module. The power module is coupled with the circuit module for providing electricity for the control unit. Wherein, the two induction ends become a close-loop when the two induction ends are in contact with the injection solution contained within the dripping pipe and when the power module supplies electricity to the induction ends; in addition, the two induction ends become an open-loop when the two induction ends are not in contact with the injection solution, and then the circuit module will detect such open-loop status and make the alarm module to generate an alarm signal.

In a preferred embodiment, each of the two induction ends is in the form of sharp-pointed probe capable of penetrating an outer surface of the dripping pipe in such a manner that, each said induction end has a detecting end penetrating into the dripping pipe for contacting the injection solution, while each said induction end further has a conductive end located outside the dripping pipe for coupling to the control unit.

In a preferred embodiment, the two induction ends are built-in the dripping pipe, each said induction end has a detecting end located inside the dripping pipe for contacting the injection solution, while each said induction end further has a conductive end located outside the dripping pipe for coupling to the control unit.

In a preferred embodiment, the dripping pipe is integrated with the alert device to become a single device; wherein the alarm module comprises one of the following: a speaker and an LED.

In a preferred embodiment, the circuit module comprises a signal output for transmitting said alarm signal to a nurse department away from the alert device.

In a preferred embodiment, the control unit further comprises a power saving module for controlling the connecting status between the power module and the circuit module, so as to control whether or not the circuit module together with the two induction ends are powered by the power module or not; wherein the power saving module comprises one of the following: a switch or an insulation plate; wherein the circuit module provides a low-power alerting mode for actuating the alarm module to generate a "low power" signal when the remaining power of the power module is lower than a predetermined level.

In a preferred embodiment, the alert device further comprises an electric-controlled valve; the valve is furnished at a predetermined location beneath the dripping pipe and is connected to a valve controlling unit of the control unit; the circuit module controls the valve to switch between an open status and a close status via the valve controlling unit, so as to control a passage of the dripping pipe.

In a preferred embodiment, when the circuit module of the control unit detects that the two induction ends are in the open-loop status, which means a water level of the injection solution remained inside the dripping pipe is below a position of the induction ends, then the circuit module controls the alarm module to generate alarm signal; and then, after a predetermined period of time, the circuit module also controls the valve controlling module to switch off the valve in order to obstruct the passage of dripping pipe so as to prevent the remaining injection solution inside the dripping pipe from completely exhausted; wherein the predetermined period of time is ranged from twenty seconds to ten minutes.

In a preferred embodiment, the power module includes at least one of the following: a replaceable battery, chargeable battery module and a transformer.

In a preferred embodiment, the alert device further comprises an elastic clip having two clipping tips. Wherein, each of the two induction ends is furnished on an end of one of the two clipping tips of the elastic clip. The elastic clip can clip on the dripping pipe, having its two clipping tips clamping on outer surface of the dripping pipe in such a manner that, the detecting ends of the two induction ends will penetrate the surface of the dripping pipe so as to make contact with the injection solution contained within the dripping pipe.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
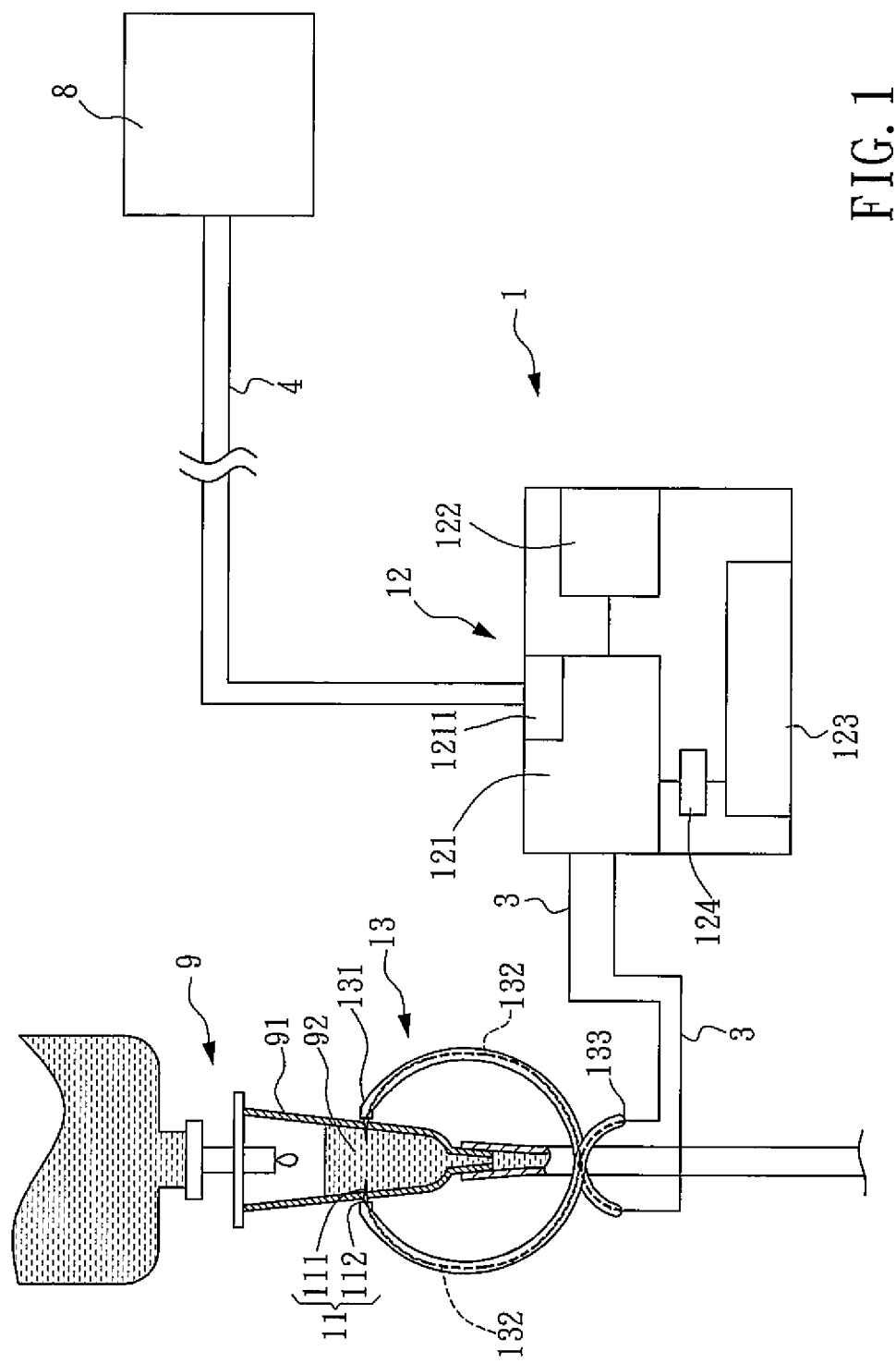
FIG. 1 schematically shows a first preferred embodiment of the alert device for intravenous drip in accordance with the present invention.

Please refer to FIG. 1, which schematically shows a first preferred embodiment of the alert device for intravenous drip in accordance with the present invention. The alert device 1 of the present invention is furnished on a dripping pipe 91 of the intravenous drip 9. The dripping pipe 91 contains some injection solution 92 dripped from a container bag located above the dripping pipe 91. The alert device 1 comprises: two induction ends 11 and a control unit 12. Each induction end 11 further comprises: a detecting end 111 and a conductive end 112. The control unit further comprises: a circuit module 121, an alarm module 122, a power module 123 and a power saving module 124.

The two induction ends 11 are respectively positioned at a predetermined location (i.e., height) of the dripping pipe 91 in such a manner that, these two induction ends 11 not only are apart from each other but also are in contact with the injection solution 92 contained inside the dripping pipe 91. That means, the user can change the fixing location (i.e., height) of the two induction ends 11 on the dripping pipe 91 in order to adjust the timing for the alarm module 122 to generate alarm signals. For example, when the two induction ends 11 are fixed to a higher location of the dripping pipe 91, then the timing will be sooner for the two induction ends 11 to lose contact with the injection solution 92, and thus the alarm module 122 will generate alarm signals sooner. In the mean time, the amount of remaining injection solution 92 inside the dripping pipe 91 is relatively more, and thus the nurse will have more time to replace a new container bag of the injection solution 92 before the dripping pipe 91 is completely empty. In contrast, when the two induction ends 11 are fixed to a lower location of the dripping pipe 91, then it will take longer time to let the two induction ends 11 to lose contact with the injection solution 92, and thus the alarm module 122 will generate alarm signals later. Therefore, by adjusting the height of the position where the two induction ends 11 are fixed on the dripping pipe 91, the buffering time for the nurse to change the container hag of injection solution 92 can be adjusted.

In a preferred embodiment of the present invention, each of the two induction ends 11 is in the form of the fine or sharp-pointed probe and is furnished on an end of one of the two clipping tips 131 of the elastic clip 13. The elastic clip 13 can clip on the dripping pipe 91, having its two clipping tips 131 clamping at the predetermined locations on outer surface of the dripping pipe 91 in such a manner that, the detecting ends 111 of the two induction ends 11 will penetrate the surface of the dripping pipe 91 so as to make contact with the injection solution 92 contained within the dripping pipe 91. Because the elastic clip 13 provides clamping force on the two clipping tips 131 while the dripping pipe 91 is made of flexible and elastic material, the injection solution 92 contained within the dripping tube 91 will not leak out due to the penetration of detecting ends 111. In addition, each induction end 11 also has a conductive end 112 connected to the detecting end 111. These two conductive ends 112 of the induction ends 11 are electrically connected to the conductive wires 132 embedded within the elastic clip 13. The conductive wires 132 then extend to the tail ends 133 of the elastic clip 13 in order to electrically connected with the cable 3 which is then connected to the circuit module 121 of the control unit 12. The elastic clip 13 is made of plastic, ceramics or metal.

The circuit module 121 of control unit 12 is coupled with the alarm module 122, and is for determining whether the two induction ends 11 are in an open-loop status (i.e., no contact with injection solution 92) or a close-loop status (i.e., still in contact with injection solution 92). The circuit module 121 can provide a low-power alerting mode for actuating the alarm module 122 to generate a "low power" signal when the remaining power of the power module 123 is lower than a predetermined level, such that the nurse can be aware of such situation and come to change the battery (or re-charge the built-in battery) of the power module 123 in time. The alarm module 122 can be a speaker or an LED flash light. The power module 123 electrically couples the circuit module and provides electricity to the control unit 12 and the two induction ends 11. The power module 123 can includes a replaceable or chargeable battery module or a transformer connected with a plug for connecting to the city grid. The power saving module 124 is for controlling the connecting status between the power module 123 and the circuit module 121, so as to control whether or not the circuit module 121 together with the two induction ends 11 will be powered by the power module 123 or not. Such that, by operating the power saving module 124 to cut off the power supply to the circuit module 121 and the induction ends 11, the electricity of the power module 123 can be saved and thus extends the operating time of the alert device 1 of the present invention. Wherein, the power saving module 124 can comprise one of the following: a switch or an insulation plate to be placed on a pole of battery.

In addition to make the alarm module 122 to generate alarm sounds or lights, when the injection solution 92 is going to run out the control unit 12 further send out an alarm signal which is transmitted to a remote nurse department 8 away from the alert device 1 through the signal output wire 4 by means of a signal output 1211 furnished in the circuit module 121. In another embodiment of the invention, the signal output 1211 of the circuit module 121 can also be a wireless communicating module such that the alarm signal can also be transmitted wirelessly to the nurse department 8. For example, the signal output 1211 can include one of the following: an infrared rays (IR) transceiver, a Bluetooth transceiver, a WiFi transceiver, a GSM transceiver os other kinds of wireless communication modules well-known in the art. Such that, the nurses in the nurse department 8 will be able to monitor the alarming status of the alert device 1 in a remote manner.

The alert device 1 for intravenous drip of the present invention uses the elastic clip 13 to clamp on the dripping pipe 91 of the intravenous drip in such a manner that, the two detecting ends 111 of induction ends 11 located on the clipping tips 131 of the elastic clip 13 will penetrate the surface of dripping pipe 91 in order to make contact with the injection solution 92 contained within the dripping pipe 91. Because the injection solution 92 is conductive, and thus the two detecting ends 111 of induction ends 11 become a close-loop when the power module 123 supply electricity to the induction ends 11 through the cable 3 and the conductive ends 112. Therefore, the circuit module 121 of control unit 12 will be able to detect such close-loop status in order to monitor the remaining injection solution 92 inside the dripping pipe 91 is either above or below a water level (i.e., height) determined by the fixing position (i.e., height) of the induction ends 11.

When the water level of the injection solution 92 remained inside the dripping pipe 91 is below (lower than) the position (height) of the two detecting ends 111 of induction ends 11, the two detecting ends 111 become open-loop because there is no injection solution 92 to be conductive media between these two detecting ends 111. Which means, the injection solution 92 is going to be exhausted. The circuit module 121 will detect such open-loop status and then make the alarm module 122 to generate alarming sounds or lights, and also generate and send out the alarm signals to the nurse department 8 through the signal output 1211 and signal output wires 4, so as to remind the nurses to change a new container bag of injection solution 92 in time.

Since the following embodiments described below have similar components and features like the one illustrated above, thus same components and structures will be assigned with the same numerals and names, while similar components and structures will be assigned with the same names but will add an additional alphabet after their numerals, and no detail descriptions will be provided for these same or similar components and structures.

Figure 2:
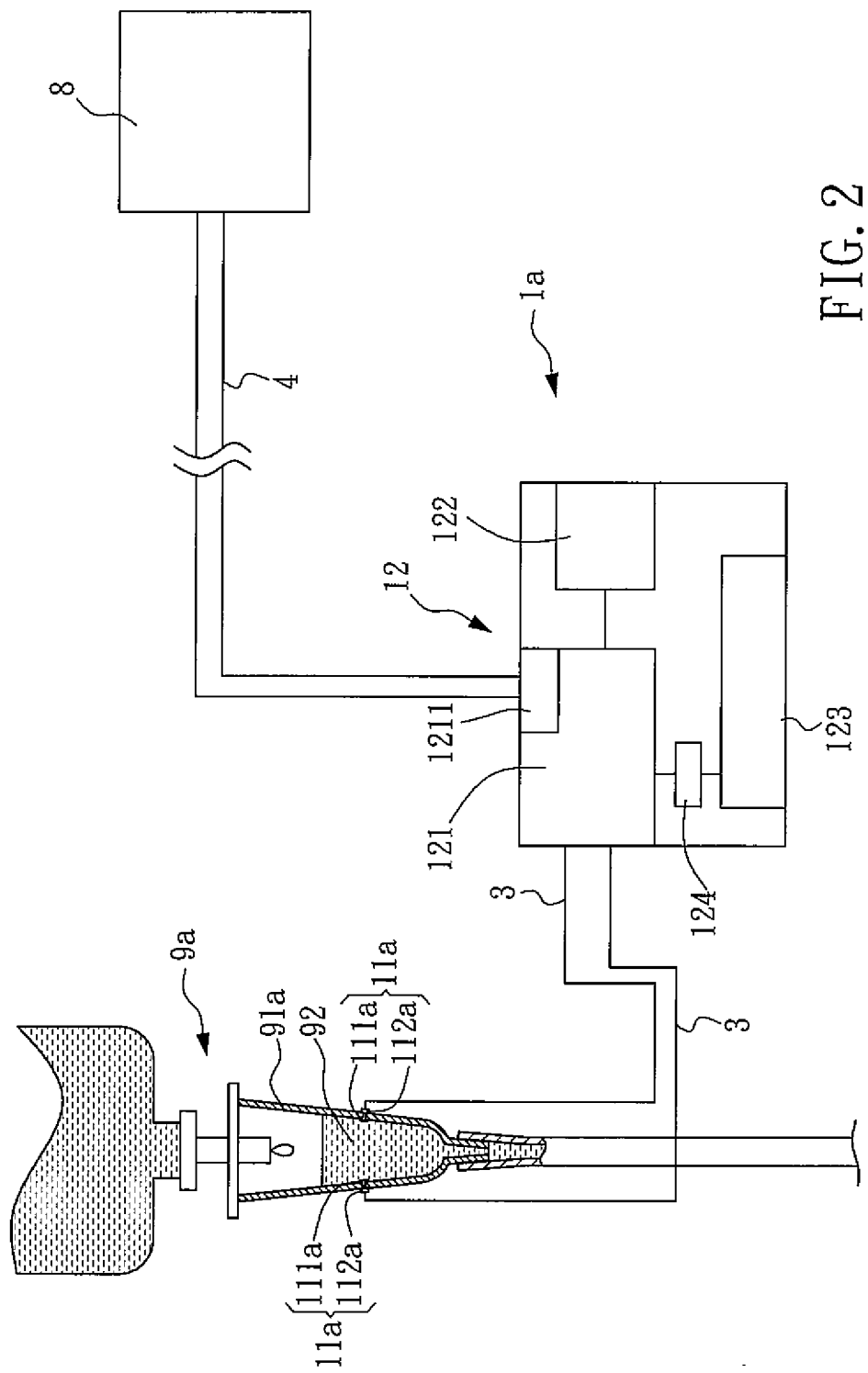
FIG. 2 illustrates a second embodiment of the alert device for intravenous drip in accordance with the present invention.

Please refer to FIG. 2, which illustrates a second embodiment of the alert device for intravenous drip in accordance with the present invention. The differences between the second embodiment shown in FIG. 2 and the first embodiment shown in FIG. 1 include: the two induction ends 11a of the alert device 1a shown in FIG. 2 are built-in the dripping pipe 91a of the intravenous drip 9a; in addition, each induction end 11a has a detecting end 111a which is located on the inner wall of the dripping pipe 91 at a predetermined position (height) in order to make contact with the injection solution 92, while the conductive ends 112a located outside the dripping pipe 91 are connected with the control unit 12 through the cable 3. That means, by connecting one end of the cable 3 to the conductive ends 112a of the induction ends 11a which are pre-mounted on the dripping pipe 91, a circuit loop can be formed between the induction ends 11a, cable 3 and control unit 12. There is no need to "clamp" the elastic clip onto the dripping pipe anymore. Therefore, the alert device 1a shown in FIG. 2 can minimize the possibility of man-made errors caused by using the detecting ends to penetrate the surface of dripping pipe.

Figure 3:
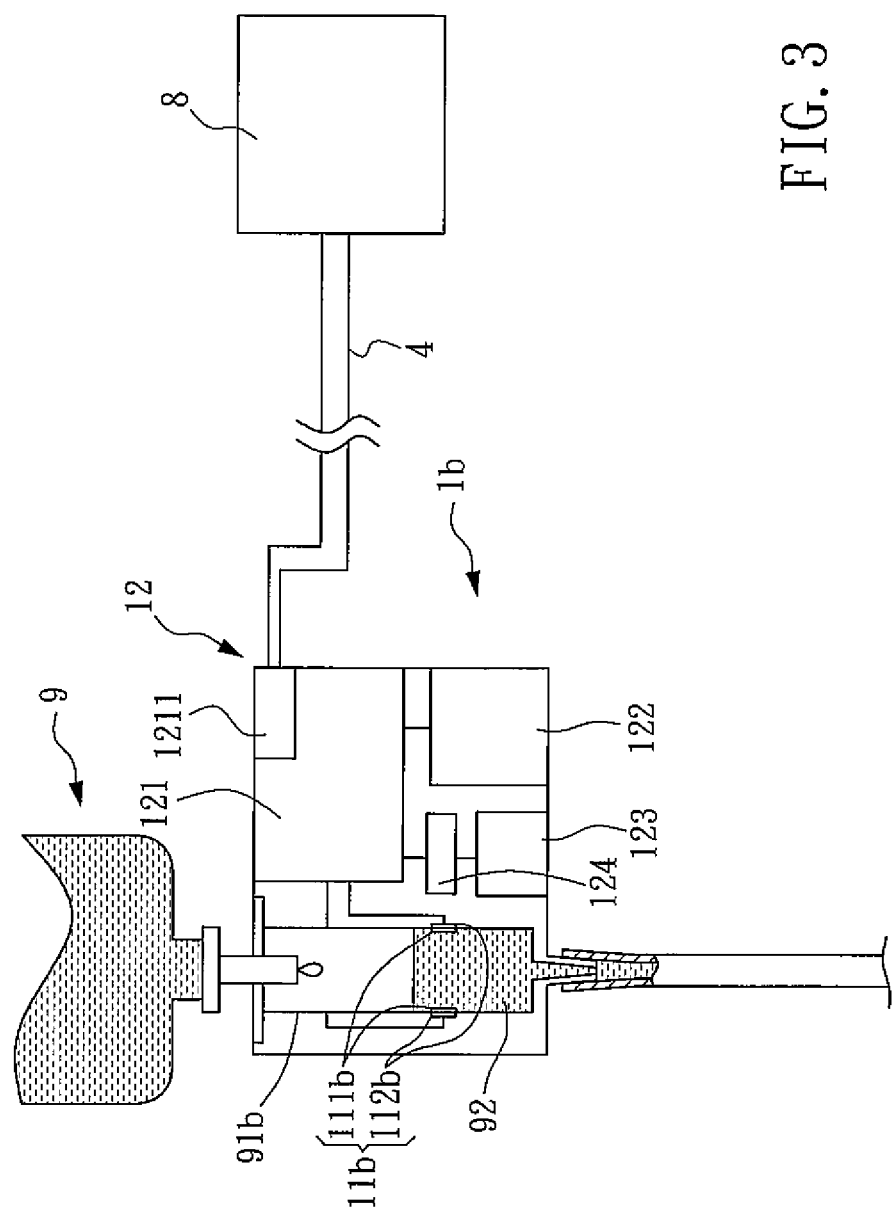
FIG. 3 illustrates a third embodiment of the alert device for intravenous drip in accordance with the present invention.

Please refer to FIG. 3, which illustrates a third embodiment of the alert device for intravenous drip in accordance with the present invention. The differences between the third embodiment shown in FIG. 3 and the first embodiment shown in FIG. 1 include: the dripping pipe 91b and the induction ends 11b are built-in the alert device 1b; and the two detecting ends 111b of the induction ends 11b are formed on the inner wall of the dripping pipe 91b, while the conductive ends 112b located outside the dripping pipe 91b are connected with the circuit module 121 of control unit 12 through the cable 3. That means, the dripping pipe 91b is integrated with the alert device 1b to become a single device, and thus no need to clamp the elastic clip onto the dripping pipe nor connecting the cable to the inductive ends, and therefore is easier to use.

Figure 4:
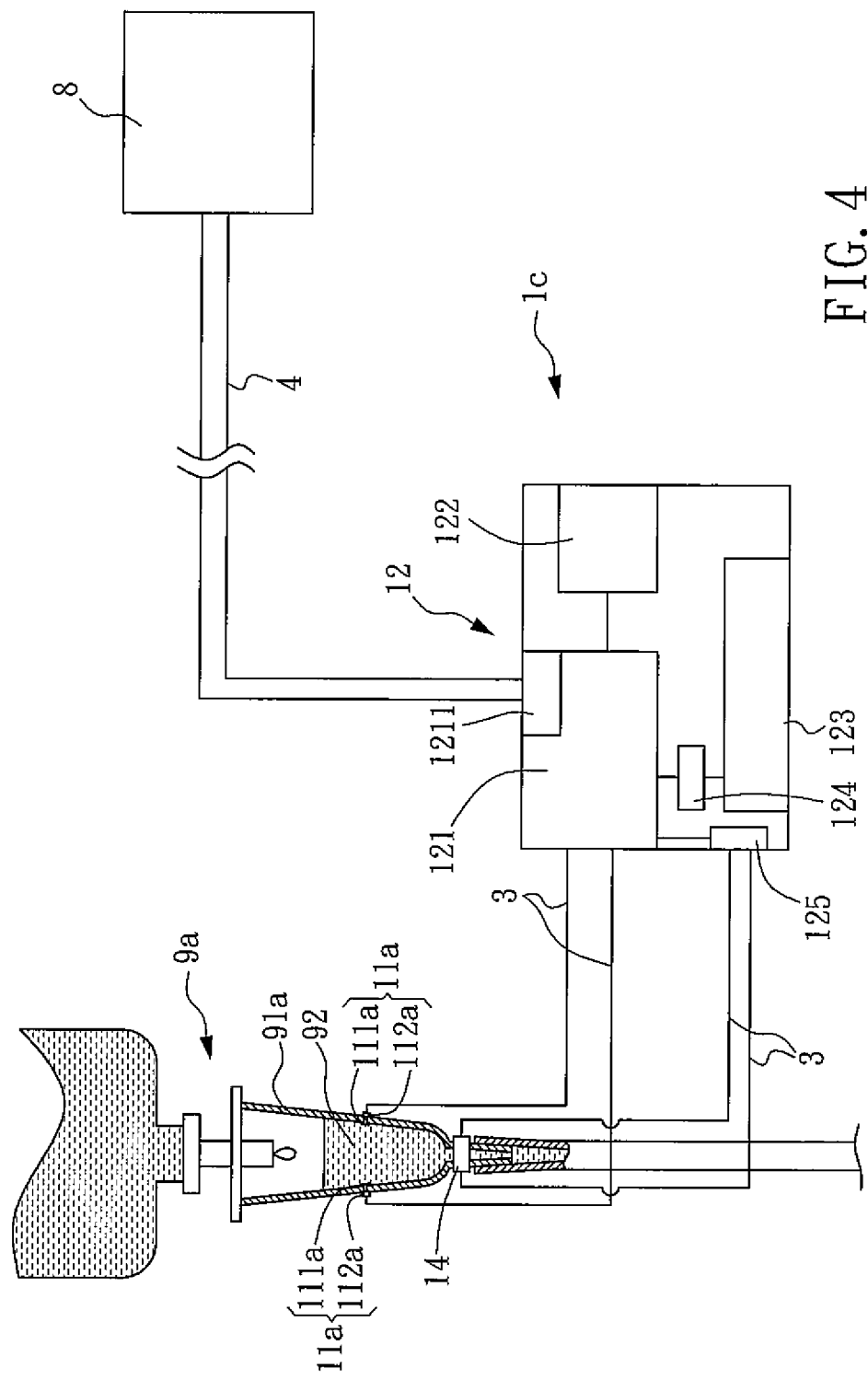
FIG. 4 illustrates a fourth embodiment of the alert device for intravenous drip in accordance with the present invention.

Please refer to FIG. 4, which illustrates a fourth embodiment of the alert device for intravenous drip in accordance with the present invention. The differences between the fourth embodiment shown in FIG. 4 and the second embodiment shown in FIG. 2 include: the alert device 1c for intravenous drip 9a further comprises a valve 14. The valve 14 is an electric-controlled valve and is furnished at a predetermined location beneath the dripping pipe 91a. The valve 14 is connected to a valve controlling unit 125 of the control unit 12 via another cable 3. The valve controlling unit 125 is coupled to the circuit module 121. The circuit module 121 can control the valve 14 to switch between an open status and a close status via the valve controlling unit 125, so as to control the passage of the dripping pipe 91a. That means, in order to avoid the incident that the injection solution 92 remained inside the dripping pipe 91a is completely exhausted, the fourth embodiment of the alert device 1c further comprises the valve 14 which is furnished at a lower end of the dripping pipe 91a. When the circuit module 121 of control unit 12 detects that the two detecting ends 111a of induction ends 11a have become open-loop, which means the water level of remaining injection solution is below the position (height) of the detecting ends 111a, then the circuit module 121 of control unit 12 controls the alarm module 122 to generate alarm sounds, lights and/or signals. And then, after a predetermined period of time, the circuit module 121 of control unit 12 also controls the valve controlling module to switch off the valve 14 in order to obstruct the passage of dripping pipe 91a, so as to prevent the remaining injection solution 92 inside the dripping pipe 91a from completely exhausted. Therefore, the risks to let the patient's blood flowing into the pipe of intravenous drip or the air entering the patient's blood vessels and causing embolisms problems caused by exhausted injection solution 92 can be minimized. In a preferred embodiment, the predetermined period of time can be ranged from twenty seconds to ten minutes, such that the nurses can have plenty of time to change the container bag.

To sum up, the present invention discloses an alert device for use with an intravenous drip. The alert device comprises two induction ends and a control unit. The control unit further comprises a circuit module, an alarm module and a power module. The two induction ends are located on a pipe of the intravenous drip and are contacting with an injection solution inside the pipe. The two induction ends are electrically connected to the control unit by wires. The circuit module detects the induction ends to determine whether the induction ends are in an open-loop status or not. The circuit module connects to the alarm module. The power module supplies power for the control unit. The induction ends uses the injection solution as an conducting means to form an electrically closed loop, as a result, when the induction ends do not contact with the injection solution, the induction ends become an open-loop, and thus the circuit module informs the alarm module to generate alarm signals before the injection solution is completely exhausted.

While the present invention has been particularly shown and described with reference to a preferred embodiment, it will be understood by those skilled in the art that various changes in form and detail may be without departing from the spirit and scope of the present invention.

I claim:

1. An alert device being attachable to a dripping pipe of an intravenous drip, the dripping pipe being able to contain an injection solution, said alert device comprising:
   at least two induction ends capable of penetrating an outer surface of the dripping pipe and contactable with the injection solution;
   an elastic clip having two clipping tips; and
   a control unit coupled with the induction ends, said control unit further comprising:
      a circuit module coupled with the induction ends for detecting whether the induction ends are in an open-loop status or a close-loop status;
      an alarm module coupled with the circuit module; and
      a power module coupled with the circuit module for providing electricity for the control unit;
   wherein each of the two induction ends is furnished on an end of one of the two clipping tips of the elastic clip; wherein each of the two induction ends is in the form of a sharp-pointed probe capable of penetrating the outer surface of the dripping pipe in such a manner that, each said induction end has a detecting end penetrating into the dripping pipe for contacting the injection solution, while each said induction end further has a conductive end located outside the dripping pipe for coupling to the control unit; wherein the elastic clip can clip on the dripping pipe, providing a clamping force on the two clipping tips and having its two clipping tips clamping on the outer surface of the dripping pipe in such a manner that, the detecting ends of the two induction ends will penetrate through the outer surface of the dripping pipe so as to make contact with the injection solution contained within the dripping pipe;
   wherein, the two induction ends become a close-loop when the two induction ends are in contact with the injection solution contained within the dripping pipe and when the power module supplies electricity to the induction ends; in addition, the two induction ends become an open-loop when the two induction ends are not in contact with the injection solution, and then the circuit module will detect such open-loop status and make the alarm module to generate an alarm signal.

2. The alert device of claim 1, wherein the circuit module comprises a signal output for transmitting said alarm signal to a nurse department away from the alert device.

3. The alert device of claim 1, wherein the control unit further comprises a power saving module for controlling the connecting status between the power module and the circuit module, so as to control whether or not the circuit module together with the two induction ends are powered by the power module or not; wherein the power saving module comprises one of the following: a switch or an insulation plate; wherein the circuit module provides a low-power alerting mode for actuating the alarm module to generate a "low power" signal when the remaining power of the power module is lower than a predetermined level; wherein, by operating the power saving module to cut off the electricity supply to the circuit module and the induction ends, the circuit module will stop detecting the status of the induction ends and thus the electricity of the power module can be saved.

4. The alert device of claim 1, wherein the power module includes at least one of the following: a replaceable battery, chargeable battery module and a transformer.

* * * * *